(12) United States Patent
Yamada

(10) Patent No.: US 8,413,483 B2
(45) Date of Patent: Apr. 9, 2013

(54) GAS SENSOR PROVIDED WITH INNER AND OUTER COVERS FOR GAS SENSING ELEMENT

(75) Inventor: Kohei Yamada, Oobu (JP)

(73) Assignee: Denso Corporation, Kariya (JP)

( * ) Notice: Subject to any disclaimer, the term of this patent is extended or adjusted under 35 U.S.C. 154(b) by 518 days.

(21) Appl. No.: 12/619,857

(22) Filed: Nov. 17, 2009

(65) Prior Publication Data

US 2010/0122569 A1    May 20, 2010

(30) Foreign Application Priority Data

Nov. 17, 2008    (JP) .................................. 2008-293591

(51) Int. Cl.
G01N 27/00    (2006.01)
(52) U.S. Cl. ....................... 73/23.31; 73/31.05; 204/428
(58) Field of Classification Search ................. 73/23.31, 73/31.05; 204/426, 428
See application file for complete search history.

(56) References Cited

U.S. PATENT DOCUMENTS

| | | | | |
|---|---|---|---|---|
| 3,960,692 | A * | 6/1976 | Weyl et al. ..................... | 204/428 |
| 4,199,424 | A * | 4/1980 | Teitelbaum ................... | 204/428 |
| 4,624,770 | A * | 11/1986 | Yamada et al. ................ | 204/428 |
| 7,758,736 | B2 * | 7/2010 | Okumura et al. ............. | 204/428 |
| 7,901,556 | B2 * | 3/2011 | Yamada ........................ | 204/428 |

FOREIGN PATENT DOCUMENTS

| | | |
|---|---|---|
| JP | H08-254521 | 10/1996 |
| JP | H09-257744 | 10/1997 |
| JP | 2003-161717 | 6/2003 |
| JP | 2003-185620 | 7/2003 |
| JP | A-2005-227179 | 8/2005 |
| JP | A-2006-058144 | 3/2006 |

* cited by examiner

*Primary Examiner* — Daniel Larkin
(74) *Attorney, Agent, or Firm* — Nixon & Vanderhye PC

(57) ABSTRACT

A gas sensor comprises a gas sensing element, a housing for the gas sensing element, and an element cover secured to an axial end of the housing and composed of an inner cover covering part of the gas sensing element and an outer cover disposed outside the inner cover. The outer cover comprise an approximately cylindrical side wall body, a bottom body integral with the side wall body, and a guide having first and second ends, the first end being secured to the side wall body and the second end being separated from the side wall body and located to provide a side opening between the second end and the side wall body. The side opening introduces a gas thereinto. A discharge opening is formed through the bottom body. The second end is recessed inward in the outer cover and is closer to the bottom body than the first end.

4 Claims, 12 Drawing Sheets

GAS SENSOR PROVIDED WITH INNER AND OUTER COVERS FOR GAS SENSING ELEMENT

CROSS-REFERENCE TO RELATED APPLICATION

This application is based on and claims the benefit of priority from earlier Japanese Patent Application No. 2008-293591 filed Nov. 17, 2008, the description of which is incorporated herein by reference.

BACKGROUND OF THE INVENTION

1. Technical Field of the Invention

The present invention relates to a gas sensor that senses the concentration of a specific gas in a gas to be measured.

2. Related Art

A gas sensor 9 as shown in FIG. 14 has been known, which senses the concentration of a specific gas in a gas to be measured (hereinafter referred to as a "measurement gas"). This type of gas sensor is disclosed, for example, in Japanese Patent Application Laid-Open Publication No. 2003-185620.

Such a gas sensor 9 includes a gas sensing element 92 that senses the concentration of a specific gas in a measurement gas, a housing 93 having an interior through which the gas sensing element 92 is passed, and an element cover 94 consisting of an inner cover 941 and an outer cover 942, which are secured to the tip end side of the housing 93.

In order to reduce the probability of getting wet with water (hereinafter referred to as "water resistance" (anti-wettability)) of the gas sensing element 92, a gas sensor 9 as shown in FIG. 15 has also been suggested. This type of gas sensor is disclosed, for example, in Japanese Patent Application Laid-Open Publication No. 2003-161717.

An element cover 94 in such a gas sensor 9 has an inner cover 941 covering a gas sensing element 92, and an outer cover 942 disposed outside the inner cover 941. The inner cover 941 has inner charge ports 941*a* formed in its side wall body and an inner discharge port 941*b* formed in its bottom body. The outer cover 942 is disposed surrounding the outer periphery of the inner cover 941 and provided with side openings 942*a* formed in its side wall body and with a discharge opening 942*b* formed in its bottom body.

As shown in FIG. 16, in forming each of the side openings 942*a*, the side wall body of the outer cover 942 is cut into substantially a "U" shape to obtain a cut piece 944 inside the "U" shape. Then, the tip end portion of the cut piece 944 is radially pressed inward so as to be bent inward about its base end portion to thereby form the side opening 942*a*.

Each side opening 942*a* is open along the U-shaped cut line. Thus, the direction to which the opening face faces, i.e. the opening direction of the opening, is adapted to have components directed toward the axial tip end side of the gas sensor 9 as well as components directed to the circumferential direction of the gas sensor 9.

However, such a conventional type gas sensor 9 has suffered from the problems as set forth below. Specifically, as mentioned above, the conventional type gas sensor 9 is formed so that the opening direction of each side opening 942*a* will additionally include the components directed to the circumferential direction. Therefore, after entry from the side openings 942*a*, water that flows through the exhaust pipe together with the measurement gas may tend to directly go into the circumferential direction through the space between the outer cover 942 and the inner cover 941 and may tend to enter into the inner cover 941 through the inner charge ports 941*a*. Therefore, there has been a concern that the gas sensing element 92 may get wet, causing cracks at the portions that have gotten wet with the water.

One measure that can be taken may be to find the best positions of the inner charge ports 941*a* in the inner cover 941 so that the gas sensing element 92 may hardly get wet. In this case, however, it is likely that the responsiveness of the gas sensor 9 may be deteriorated.

SUMMARY OF THE INVENTION

The present invention has been made in light of the problem described above and has as its object to provide a gas sensor which is able to prevent the occurrence of cracks in the gas sensing element, which would be caused by getting wet with water, while ensuring the responsiveness of the gas sensing element.

It should be appreciated that, throughout the specification, when a term "tip end side" is used, the term refers to the side from which the gas sensor is inserted into an exhaust pipe such as of an internal combustion engine, which side corresponds to the lower side as viewed in each vertical cross-sectional view of the accompanying drawings. Also, when a term "tip end portion" is used, the term refers to the portion on the tip end side of the component concerned, which portion corresponds to the lower portion of the component concerned as viewed in each vertical cross-sectional view of the accompanying drawings.

Likewise, when a term "base end side" is used, the term refers to the side opposite to the tip end side, which side corresponds to the upper side as viewed in each vertical cross-sectional view of the accompanying drawings. Also, when a term "base end portion" is used, the term refers to the portion on the base end side of the component concerned, which portion corresponds to the upper portion of the component concerned as viewed in each vertical cross-sectional view of the accompanying drawings.

Further, throughout the specification, when a term "axially" or "in the axial direction" is used, the term refers to the axial direction of the gas sensor concerned. The axial direction of the gas sensor corresponds to the vertical direction in each vertical cross-sectional view of the accompanying drawings.

In order to realize the above object, there is provided a gas sensor comprising a gas sensing element that senses a concentration of a specific gas within a gas to be measured, length-wise directions of the gas sensing element being defined as an axial direction, directions extending radially from the gas sensing element along a plane perpendicular to the axial direction being defined as a radial direction, and directions perpendicular to both axial and radial directions being defined as a circumferential direction. The gas sensor also comprises a housing that houses the gas sensing element in a state where the gas sensing element passes through a bore of the housing; and an element cover secured to an end of the housing in the axial direction such that the element cover covers part of the gas sensing element which extends from the housing. The element cover comprises an inner cover covering the part of the gas sensing element and at least one outer cover disposed outside the inner cover, the at least one outer cover comprising a first charge port that allows the gas to be measured to be introduced thereinto. The inner cover comprises a second charge port that allows the gas to be measured, which has been introduced through the first charge port, to be introduced thereinto and a discharge port that discharges the gas to be measured, from an inside of the inner cover to an outside of the gas sensor, the at least one outer cover includes a drain cover that drains water from an inside thereof to an outside thereof which is the outside of the gas sensor, the drain cover comprises an approximately cylindrical side wall body disposed in parallel with the axial direction, a bottom body integral with an end of the side wall body which is opposite to the end of the housing, and a guide having first and second end, the first end being secured to the side wall body and the second end being separated from the side wall body and located to provide a side opening between the second end and the side wall body, the side opening functioning as the first charge port, a discharge opening being formed through the bottom body, and the second end of the guide is recessed inward in the drain cover and is closer to the bottom body than the first end of the guide. For example, the side opening consists of a plurality of side openings located in the circumferential direction.

Hereinafter, the advantages of the present embodiment will be described.

The side openings (orifices) are each provided with a guide protruded in the radial direction of the gas sensor and with an opening defined by the edge of the guide. Each of the guides introduces water so as to be directed to the axial tip end side, without permitting the water to be directed to the circumferential direction of the gas sensor or toward the inner charge ports. The inventors of the present invention have found that this configuration can prevent the gas sensing element from getting wet with water and thus can prevent cracks from occurring in the gas sensing element due to the water, while ensuring the responsiveness of the gas sensing element.

The side openings according to the conventional art have been formed such that the opening direction of each of the side openings will have the components directed not only to the axial tip end side but also to the circumferential direction. Therefore, the water that has entered into the outer cover together with the measurement gas may directly into the circumferential direction and enter into the inner cover from the inner charge ports, causing cracks in the gas sensing element.

In this regard, with the present embodiment, the side openings are each formed such that the guide thereof can direct water to the axial tip end side, without permitting the water to be directed to the circumferential direction of the gas sensor or toward the inner charge ports. Accordingly, water as mentioned above can be sufficiently suppressed from moving in the circumferential direction in the interior of the drain cover and from being directly directed to the inner charge ports.

Further, the side openings each have the opening direction which is imparted with the components directed to the axial tip end side. Accordingly, water that has flowed with the measurement gas will first enter into the interior of the drain cover from the side openings, but then will be directly directed, relatively linearly, to the tip end side with the force of inertia and discharged from the discharge opening.

In the present embodiment, in particular, since the opening direction does not have the components directed to the circumferential direction, water can be forcibly directed to the tip end side, whereby the advantageous effect as mentioned above can be remarkably exerted.

As a result, water can be well prevented from entering into the interior of the inner cover to well prevent the occurrence of cracks in the gas sensing element due to the water.

Meanwhile; the measurement gas having specific gravity comparatively smaller than the water will first enter into the interior of the drain cover together with the water. Then, a part of the measurement gas will flow relatively linearly with the water toward the discharge opening, while a part of the measurement gas will flow separate from the water. The measurement gas that has flowed separate from the water will flow, in a curve, toward the direction opposite to the discharge opening, i.e. toward the base end side. Thus, the interior of the drain cover will be sufficiently filled with the measurement gas. Accordingly, the measurement gas can be well introduced to each of the inner charge ports and thus can be well introduced to the gas sensing element.

As a result, responsiveness similar to that of the gas sensor based on the conventional art can be ensured.

As described above, with the gas sensor according to the present invention, cracks can be prevented from occurring in the gas sensing element due to getting wet with water, while the responsiveness of the gas sensing element can be ensured.

The gas sensor of the present invention may be installed in an exhaust pipe of an internal combustion engine of various types of vehicles, such as an automotive engine, for use, for example, as: an air-fuel ratio sensor (A/F sensor) for an exhaust gas feedback system; an oxygen sensor ($O_2$ sensor) that measures the oxygen concentration of an exhaust gas; or an NOx sensor that checks the concentration of an air pollutant, such as NOx, and is utilized for detecting deterioration of three-way catalyst disposed in the exhaust pipe.

In the drain cover, the side openings function as the outer charge ports.

In the present invention, the opening face defined by the profile line of each side opening is formed so as to have substantially a planar face. Accordingly, a side opening as shown in FIG. 16, for example, having a curved opening face and not having substantially a planar face is not included in the present invention.

Further, the above expression "without permitting the water to be directed to the circumferential direction of the gas sensor or toward the inner charge ports" implies that it may be satisfactory if only the opening direction of each of the side openings is not essentially oriented to the inner charge ports, even when the side openings and the inner charge ports are positioned at substantially the same level with respect to the axial direction of the gas sensor.

It is preferred that the one or more outer covers are composed of only the drain cover.

With such a simple structure, the gas sensor of the present embodiment can reduce the cost, and can prevent the gas sensing element from getting wet with water and thus can prevent the occurrence of cracks in the gas sensing element due to the water, while ensuring its responsiveness.

It is also preferred that the side opening has an opening direction having a directional component directed toward only the bottom body in the axial direction.

Thus, water that flows with the measurement gas first enters into the drain cover and then will mostly be discharged from the discharge opening. Accordingly, the gas sensor of the present invention can prevent the occurrence of cracks in the gas sensing element that would be caused by getting wet with water.

Preferably, the side opening has an opening direction having a directional component directed toward only the discharge port.

Thus, since water can be more easily discharged from the discharge opening, the gas sensor of the present invention is less likely to suffer from cracks in the gas sensing element, which would be caused due to getting wet with water.

Preferably, the side wall body is composed of a plate-like material and the guide is composed of a plate segment having the first and second ends, wherein the plate segment is integral with the side wall body and the side opening is an opening formed by the plate segment through the side wall body.

Thus, the drain cover can be formed without using additional members, to thereby enhance the productivity of the gas sensor of the present invention.

Preferably, the side wall body is cut at a position thereof corresponding to the second end of the plate segment and the plate segment is recessed inward in the radial direction such that the plate segment is bent obliquely to the axial direction to produce a recess, the first end of the plate segment is kept to be integral with the side wall body, and the side opening is formed between the second end of the plate segment which is cut and a cut edge of the side wall body, the second end of the plate segment being closer to the bottom body than the first end thereof.

Thus, the side openings and the respective guides can be easily formed by unidirectionally cutting the side wall body, followed by inwardly pressing the cut portion using a pressing jig that has a shape inverse of that of the guide.

Still preferably, the recess formed by the plate segment is formed to have an approximately triangular shape when being viewed in the radial direction, the recess being widened gradually in both the radial and circumferential directions as an axial position of the plate segment comes closer to the bottom body.

Thus, the measurement gas and water can be introduced into the drain cover along the shape of the guide, whereby the advantageous effect of the present invention can be more effectively exerted.

It is preferred that the guide member is located to shadow the inside the drain cover when being viewed in the radial direction.

Thus, the measurement gas and water will not be introduced into the element cover from the direction perpendicular to the axial direction of the gas sensor. Accordingly, the measurement gas and water can be forcibly directed to the axial direction. In this way, water can be suppressed from being directed to the circumferential direction in the space between the outer cover and the inner cover, whereby the advantageous effect of the present invention can be remarkably exerted.

It is preferred that the side opening has an radial opening depth defined by a maximum distance of the side opening in the radical direction and an axial opening height defined by the a maximum distance of the side opening in the axial direction, wherein the radial opening depth is 1.5 mm or less and the axial opening height is 0.6 mm or less.

Thus, the gas sensor of the present invention can further prevent the occurrence of cracks in the gas sensing element, which would be caused due to getting wet with water.

On the other hand, if the opening depth is less than 1.5 mm and the opening height is more than 0.6 mm, it may be difficult to obtain a gas sensor having higher water resistance.

For example, the radial opening depth is 0.5 mm or more.

Thus, the gas sensor of the present invention can have good responsiveness.

For example, the side opening is positionally closer to the bottom body than the second charge port in the axial direction.

Thus, water and a part of the measurement gas are relatively linearly directed to the discharge opening, while most of the a measurement gas separated from the water is directed, drawing a curve, toward the base end side and then is introduced into the inner cover from the inner charge ports. Therefore, the gas sensor is well ensured with water resistance, and at the same time, will have good responsiveness.

DETAILED DESCRIPTION OF THE PREFERRED EMBODIMENTS

With reference to FIGS. 1 to 6, hereinafter will be described a gas sensor according to an embodiment of the present invention.

Figure 1:
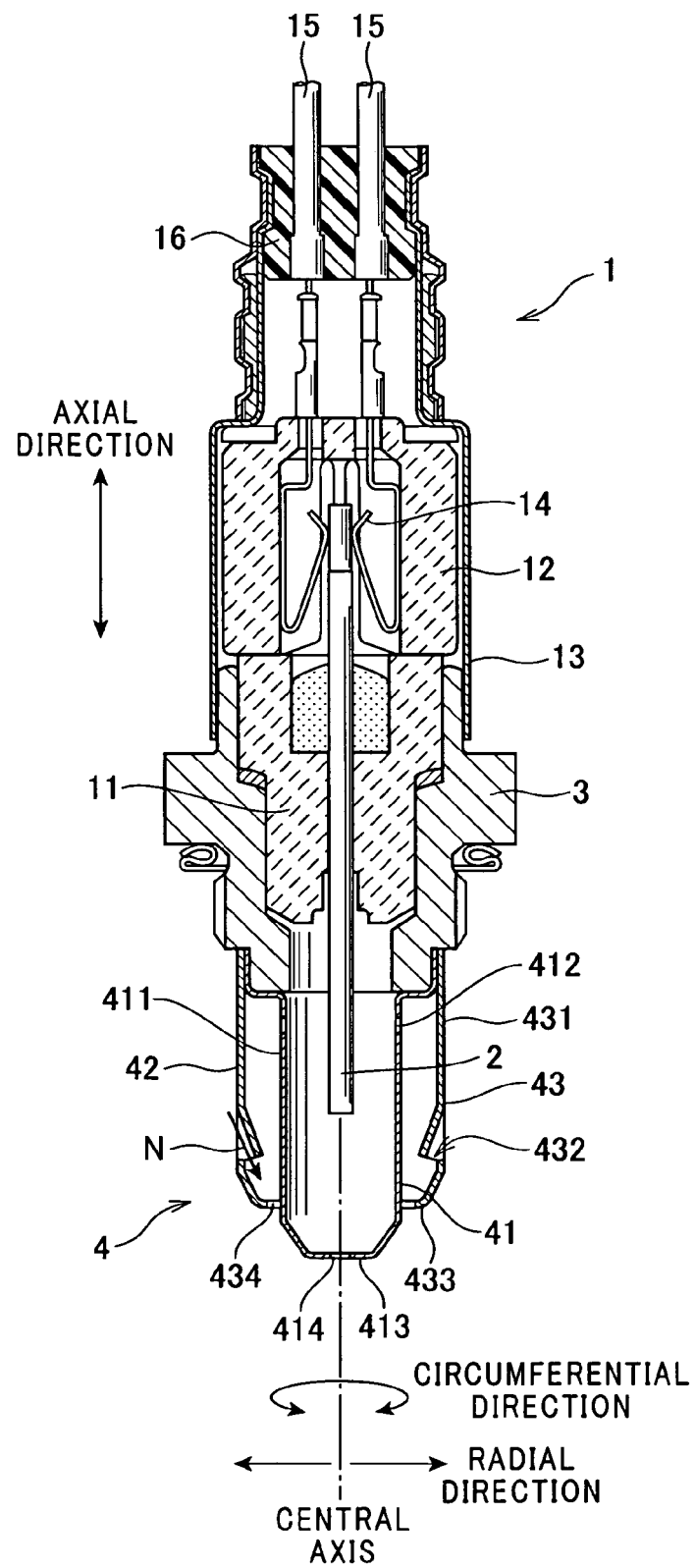
FIG. 1 is a vertical cross-sectional view illustrating a gas sensor according to an embodiment of the present invention.
Figure 2:
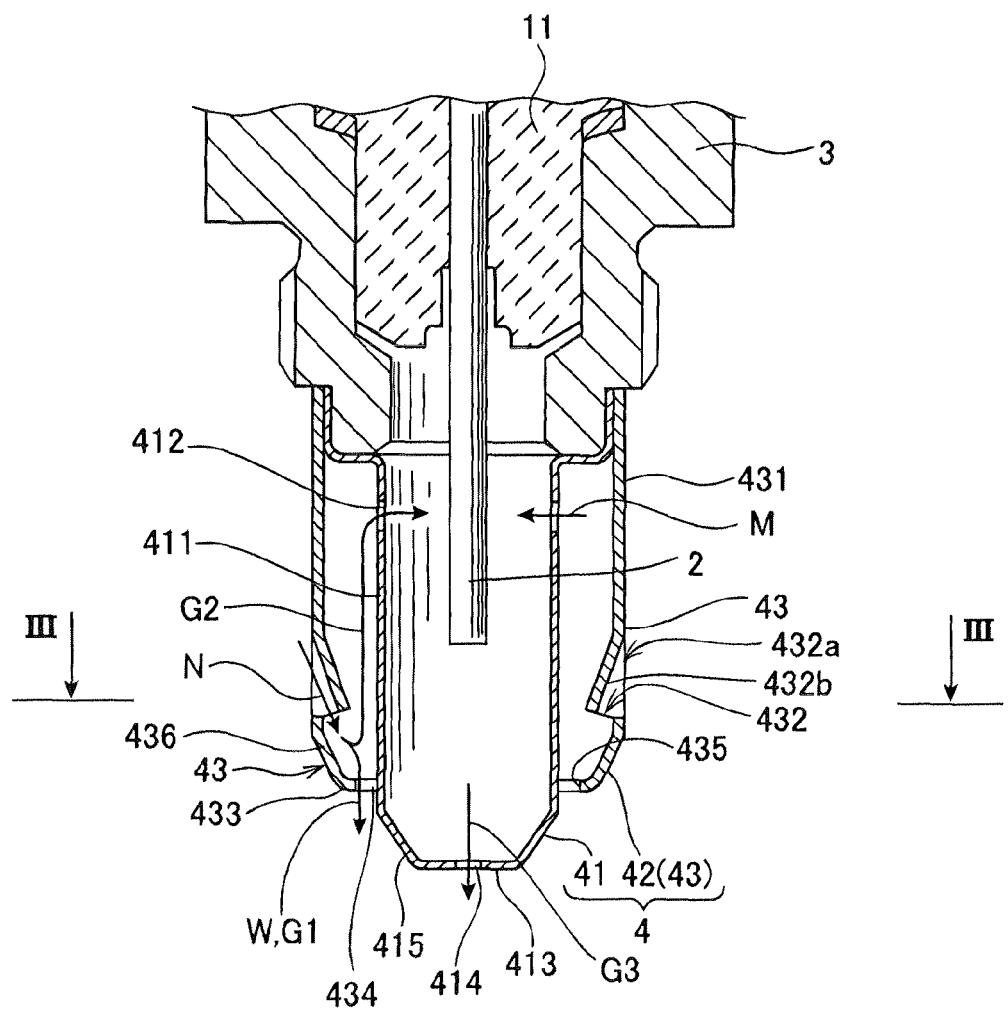
FIG. 2 is a vertical cross-sectional view illustrating a tip end portion of the gas sensor according to the embodiment.

FIGS. 1 and 2 show the structure of a gas sensor 1 according to the present embodiment.

This gas sensor 1 is formed as a whole into an approximately cylindrical long member that provides a length in its longitudinal direction. Hence, in the present embodiment, as shown in FIG. 1, axial, radial and circumferential directions can be defined as below. The longitudinal direction of the gas sensor 1 is referred to as an axial direction(s), directions that extend radially from a central axis of the gas sensor 1, which is located at the center in a section perpendicular to this axial direction, are referred to as a radial direction(s), and directions perpendicular to both axial and radial directions, that is, directions that run around the central axis along the perpendicular plane, are referred to as a circumferential direction(s).

As shown in FIGS. 1 and 2, the gas sensor 1 is provided with a gas sensing element 2, a housing 3, and an element cover 4. The gas sensing element 2 is formed as a stick-shaped long member and produced to sense the concentration of a specific gas in a gas to be measured (hereinafter, referred to as a measurement gas), and output an electric signal indicative of an amount of sensed concentration. The length-wise direction of the gas sensing element 2 is along the axial direction: when being incorporated in the gas sensor 1.

The housing 3 is produced to have a bore and house the gas sensing element 2 so that the housing 2 allows the gas sensing element to pass through the bore of the housing along the axial direction. The element cover 4 is secured to one end of the housing 3 in the axial direction and formed to cover part of the gas sensing element 2 which extends from the housing 3 in the axial direction.

The element cover 4 has an inner cover 41 covering the gas sensing element 2 and has a single outer cover 42 disposed outside the inner cover 41.

In other words, in the gas sensor 1 of the present embodiment, the element cover 4 has a double structure consisting of the inner cover 41 and the outer cover 42 serving as a drain cover 43.

Alternatively, the outer cover 42 may be composed of a plurality of outer covers that includes a single drain cover 43.

The inner cover 41 has a cylindrical side wail body 411 (hereinafter just referred to as a "side wall body 411") and a bottom body 413 formed at the tip end portion of the side wall body 411. The outer cover 42 serving as the drain cover 43 has a cylindrical side wail body 431 (hereinafter just referred to as a "side wall body 431") and a bottom body 433 formed at the tip end portion of the side wall body 431.

The inner cover 41 has inner charge ports 412 which introduce a measurement gas into the interior of the inner cover 41 and has an inner discharge port 414 which discharges the measurement gas introduced into the inner cover 41.

The drain cover 43 that is the outer cover 42 has side openings (orifices) 432 and a discharge opening (orifice) 434.

The side openings 432 are formed in the side wall body 431 to introduce the measurement gas into the drain cover 43. Each of the side openings 432 is formed by providing a guide 432a being protruded in the radial direction of the gas sensor 1, with each opening 432 being defined by the edge of the guide 432a (see FIG. 4A).

The discharge opening 434 is arranged at the bottom body 433 to discharge the measurement gas introduced into the drain cover 43.

As shown in FIGS. 1 to 4B, each of the side openings 432 is formed so that an opening direction N directed from the exterior of the drain cover 43 to the interior thereof includes components directed to the tip end side in relation to the axial direction of the gas sensor 1.

Specifically, in the present embodiment, the opening direction N does not include the components directed to the circumferential direction. That is, each of the side openings 432 is formed such that the opening direction N will only have the components directed to the discharge opening 434.

More specifically, the side openings 432 are each formed such that the guide 432a thereof can introduce water to the axial tip end side, without permitting the water to be introduced to the circumferential direction of the gas sensor 1 or toward the inner charge ports 412.

Each of the inner charge ports 412 of the inner cover 41 is ensured not to align with any side opening 432. As will be described later, the inner charge ports 412 are each arranged near the base end side in relation to the side openings 432.

Further, in the gas sensor 1 of the present embodiment, each opening face defined by the profile line of the side opening 432 is formed so as to have substantially a planar face.

The details will be described hereinafter.

The gas sensor of the present embodiment may be installed in an exhaust pipe of an internal combustion engine of various types of vehicles, such as an automotive engine, for use, for example as: an air-fuel ratio sensor (A/F sensor) for an exhaust gas feedback system; an oxygen sensor ($O_2$ sensor) that measures the oxygen concentration of an exhaust gas; or an NOx sensor that checks the concentration of an air pollutant, such as NOx, and is utilized for detecting deterioration of three-way catalyst disposed in an exhaust pipe.

As described above, the gas sensor 1 of the present embodiment includes the gas sensing element 2, the housing 3 and the element cover 4. Also, as shown in FIG. 1, the gas sensor 1 includes an element-side insulation porcelain 11, an air-side insulation porcelain 12, an air-side cover 13, metal terminals 14, external leads 15 and a bush 16, which will be described later.

The gas sensing element 2 is made up of a solid electrolyte body mainly containing zirconia and provided with a reference-gas-side electrode on one surface and a measurement-gas-side electrode on the other surface (not shown). The gas sensing element 2 is incorporated with a heater (not shown) to heat the gas sensing element 2 up to as high as 400° C. or more for activation when the gas sensor 1 is in use.

Although the gas sensing element 2 used in the present embodiment is of a stacked type, a bottomed and cup-shaped cylindrical gas sensing element may alternatively be used.

As shown in FIGS. 1 and 2, the housing 3 holds therein the element-side insulation porcelain 11 through which the gas sensor element 2 is inserted being held thereby.

The element-side insulation porcelain 11 has a base end side which is provided with the air-side insulation porcelain 12 to cover the base end portion of the gas sensing element 2. The air-side cover 13 is arranged covering the air-side insulation porcelain 12 and secured to the base end portion of the housing 3.

The metal terminals 14 for establishing electrical conduction with the gas sensing element 2 are held inside the air-side insulation porcelain 12.

The external leads 15 connected to the respective metal terminals 14 are arranged passing through the bush 16 that chokes the base end portion of the air-side cover 13.

As mentioned above, the element cover 4 has a double structure consisting of the inner cover 41 and the drain cover 43 that is the outer cover 42. In the following description, the outer cover 42 will be referred to as the drain cover 43.

As mentioned above, the inner cover 41 has the side wall body 411 and the bottom body 413.

The inner charge ports 412 of the inner cover 41 are punched at the base end side of the side wall body 411 to introduce a measurement gas into the interior of the inner cover 41. The inner discharge port 414 of the inner cover 41 is formed in the bottom body 413 to discharge the measurement gas to the exterior of the inner cover 41. As shown in FIGS. 1 and 2, the inner charge ports 412 are each formed near the base end side in relation to the side openings 432.

The inner cover 41 also has a single inner diameter-change portion 415 having a tapered shape, which reduces its diameter toward its tip end side.

As shown in FIG. 2, each of the inner charge ports 412 is formed so that an opening direction M will be directed from the exterior of the inner cover 41 to the interior thereof, i.e. will be inwardly directed in the radial direction of the gas sensor 1.

For example, six inner charge ports 412 can be formed in the side wall body 411 along the circumferential direction thereof.

The inner discharge port 414 has an inner diameter $\phi 1$ that falls within the range, for example, of 0.4 to 2.0 mm and has its opening direction parallel to the axial direction.

As mentioned above, the drain cover 43 has the side wall body 431 and the bottom body 433.

The drain cover 43 is provided, at the bottom body 433 thereof, with a tip end side discharge port 435 having an inner diameter larger than that of the side wall body 411 at the base end side of the inner diameter-change portion 415. Thus, the discharge opening 434 is formed between the discharge port 435 and the side wall body 411 of is the inner cover 41.

As mentioned above, the drain cover 43 has the side wall body 431 provided with the side openings 432.

Each of the side openings 432 is formed so that the opening direction N will have the components only directed to the discharge opening 434.

The details of the side openings 432 will be described.

Figure 3A:
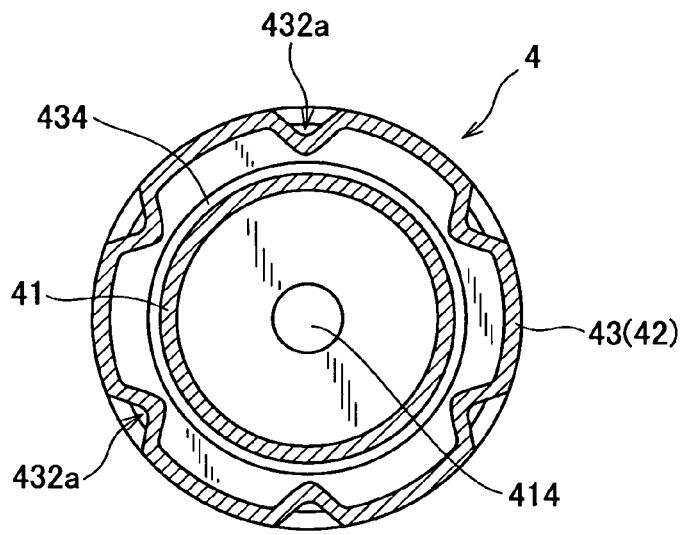
FIG. 3A is a cross-sectional view taken along line III-III of FIG. 2.
Figure 4A:
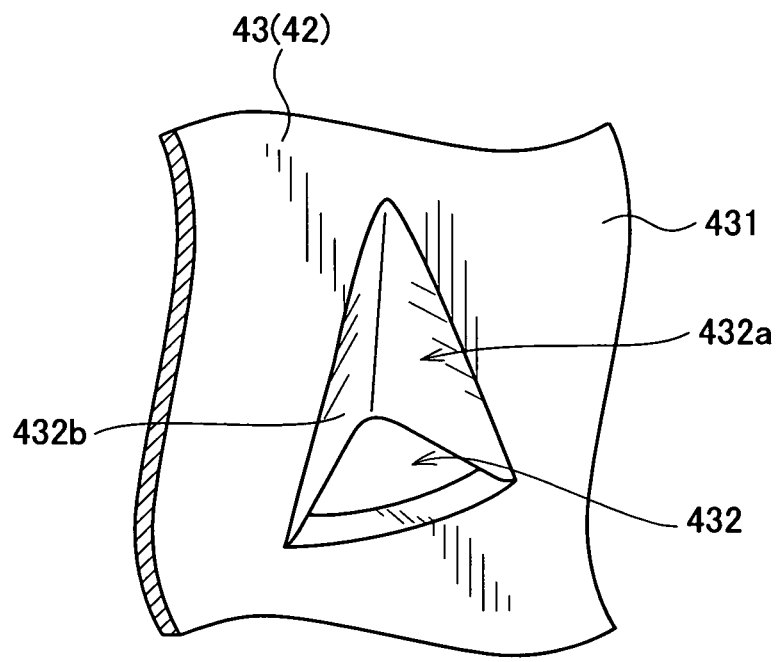
FIG. 4A is a perspective view illustrating a side opening according to the embodiment.
Figure 4B:
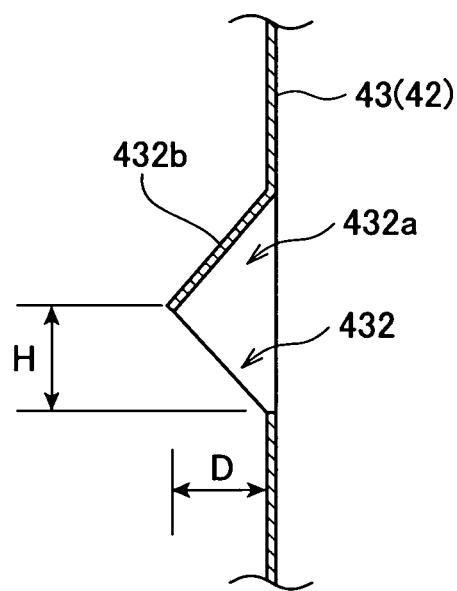
FIG. 4B is a vertical cross-sectional view illustrating the side opening according to the embodiment.

As shown in FIG. 1 and in greater detail in FIG. 3A as well as FIGS. 4A and 4B, the drain cover 43 is provided with the side openings 432 each of which is formed by permitting the side wall body 431 to be inwardly protruded in the radial direction of the drain cover 43 to thereby provide the guide 432a.

Each guide 432a has an edge defining the opening 432 at the tip end portion thereof.

As shown in FIG. 4B, each guide 432a has a profile line 432b as appears in its cross section parallel to the above axial direction. As shown in FIGS. 4A and 4B, each guide 432a is formed so that the profile line 432b will be inwardly protruded in the radial direction of the gas sensor 1 as the profile line 432b nears the tip end side of the guide 432a.

Figure 3B:
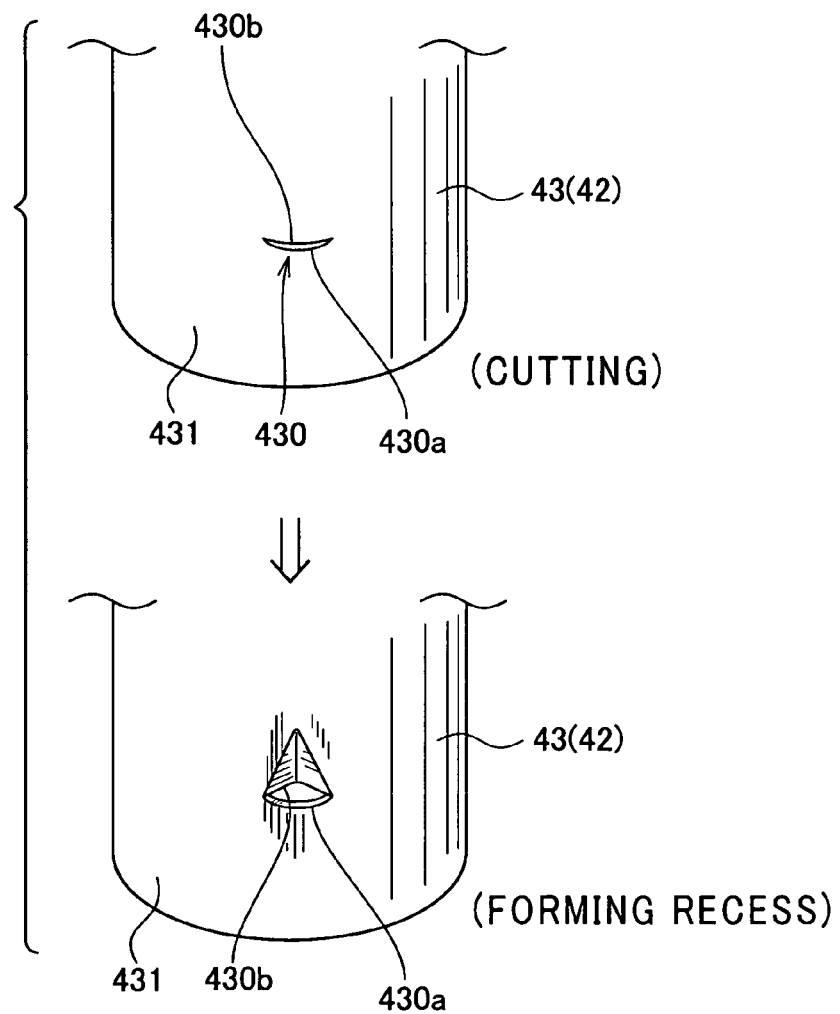
FIG. 3B is a perspective explanatory view illustrating fabrication of a drain cover.

As shown in FIG. 3B, in forming the guide 432a, the side wall body 431 is unidirectionally cut in a direction perpendicular to the axial direction to form a cut portion 430 having a tip end portion 430a and a base end portion 430b. Then, the base end portion 430b is inwardly pressed in the radial direction for deformation using a pressing jig (not shown), for example, having a substantially triangular pyramid shape. The side opening 432 is defined by the tip end portion 430a that forms the edge of the guide 432a and by the base end portion 430b of the cut portion 430.

As shown in FIG. 2, the drain cover 43 has an outer diameter-change portion 436 having a tapered shape, which reduces its diameter toward its tip end side.

For example, eight side openings 432 can be formed in the side wall body 431 near the base end side in relation to the outer diameter-change portion 436, along the circumferential direction of the side wall body 431.

As shown in FIG. 4B, each side opening 432 has an opening depth D of 1.5 mm or less. The opening depth D corresponds to the length from the radially outermost side portion of the gas sensor 1 to the radially innermost side portion thereof. Further, each side opening 432 has an opening height H of 0.6 mm or less. The opening height H corresponds to the length from the axially very base end portion of the side opening 432 to the axially very tip end portion thereof.

The drain cover 43 may have a thickness such as of 0.3 to 0.7 mm. The inner cover 41 may also have a thickness such as of 0.3 to 0.7 mm.

If the drain cover 43 has a thickness of less than 0.3 mm, sufficiently satisfactory guides 432a may not be formed or the resultant guides 432a may be less well-defined due to being less strength. On the other hand, if the drain cover 43 has a thickness of more than 0.7 mm, the life of the pressing jig used for forming the side openings 432 will be shortened, providing a factor of increasing the cost.

As shown in FIGS. 1 and 2, with the element cover 4 of the present embodiment, the center axis of the inner discharge port 414 is configured to align the center axis of the discharge opening 434.

In addition, the element cover 4 has a base end portion which is secured to the tip end portion of the housing 3. In other words, the inner cover 41 and the drain cover 43 have base end portions which are overlapped with each other, and these overlapped base end portions are secured to the tip end portion of the housing 3 such as by welding.

It should be appreciated that, alternative to the above, the inner cover 41 and the drain cover 43 may be caulked with the tip end portion of the housing 3 for fixation.

Referring to FIG. 2, hereinafter is described a pathway of a measurement gas in the gas sensor 1 according to the present embodiment.

The gas sensor 1 of the present embodiment is disposed (not shown) perpendicular to the flow direction of the measurement gas flowing through the exhaust pipe such as of an automotive engine.

In such an exhaust pipe, the measurement gas flows substantially parallel to the axial direction of the exhaust pipe. The measurement gas is introduced into the drain cover 43 from the side openings 432 of the drain cover 43.

As shown in FIG. 2, of the flows of the measurement gas introduced from the side openings 432, a flow (G1) directed to the discharge opening 434 turns to a relatively linear flow, while a flow (G2) entering from each of the inner charge ports 412 and directed to the interior of the inner cover 41 turns to a curved flow.

Accordingly, a part of the measurement gas introduced between the drain cover 43 and the inner cover 41 is directed to the discharge opening 434 (see G1) and directly discharged outside from the discharge opening 434.

On the other hand, the measurement gas that has flowed, in a curve, toward the base end side is introduced into the interior of the inner cover 41 from each inner charge port 412 (see G2).

Then, the measurement gas introduced into the interior of the inner cover 41 (see G2) is discharged outside, passing through the inner charge ports 412 and the inner discharge port 414 (see G3).

At this time, the measurement gas introduced into the inner cover 41 is sufficiently supplied to the gas sensing element 2.

Referring to FIG. 2, hereinafter is described a discharge pathway of the water contained in the measurement gas which is introduced from the side openings 432.

Each of the side openings 432 has the opening direction N which is not imparted with components directed to the circumferential direction. That is, as mentioned above, the side openings 432 are each formed such that the guide 432a thereof can introduce water to the axial tip end side, without permitting the water to be introduced to the circumferential direction of the gas sensor 1 or toward the inner charge ports 412.

Therefore, the water contained in the measurement gas and introduced from each side opening 432 will not go into the circumferential direction in the space between the inner cover 41 and the drain cover 43. Specifically, as indicated by an arrow W in FIG. 2, the water is permitted to flow together with the flow of a part of the measurement gas (G1), directed to the tip end side with the force of inertia and directly discharged outside from the discharge opening 434.

Accordingly, the water can be suppressed from being introduced into the interior of the inner cover 41 from the inner charge ports 412.

It should be appreciated that the present invention is not limited to the configuration of the gas sensor 1 of the present embodiment. For example, although not shown, the opening direction M of each inner-side charge port 412 of the inner cover 41 may be directed to the axial direction instead of the radial direction.

The inner diameter-change portion 415 or the outer diameter-change portion 436 used in the present embodiment are not essential components of the present invention.

Figure 5A:
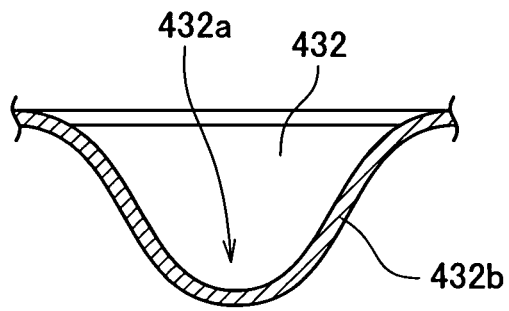
FIGS. 5A to 5C are cross-sectional views each illustrating a guide of a different mode according to the embodiment.
Figure 5B:
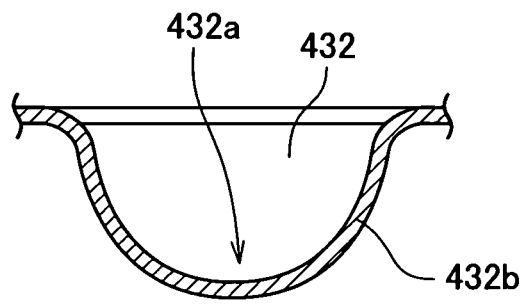
Figure 5C:
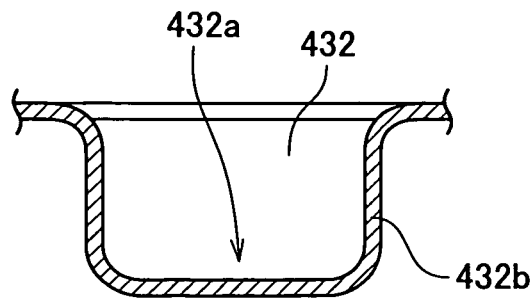

Also, the guides 432a inwardly protruded in the radial direction are not limited to the ones used in the present embodiment, but may be the ones each having a mound-shaped inward protrusion, a substantially semicircular inward protrusion or a substantially square inward protrusion. FIGS. 5A to 5C show these mound-shaped guide, substantially semicircular guide and substantially square guide, respectively, as viewed along the axial direction as in the cross-sectional view shown in FIG. 3A.

Figure 6:
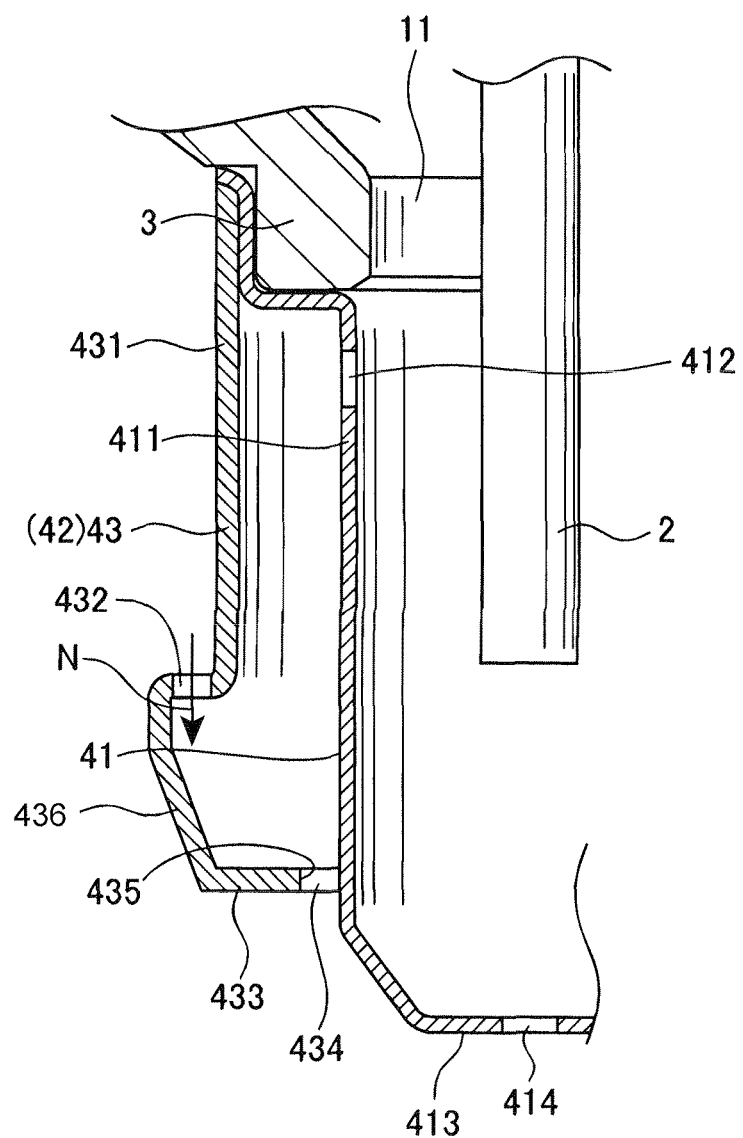
FIG. 6 is a vertical cross-sectional view illustrating a tip end portion of a gas sensor having an element cover according a modification of the embodiment.

FIG. 6 shows a modification of the present embodiment. Specifically, as can be seen from the modification, the side openings 432 may be formed in a base end face of a diameter expanded portion 436 formed in the side wall body 431. In this case, the base end face of the diameter expanded portion 436 should be formed parallel to the axial direction, so that that the opening direction N can be necessarily imparted with the components directed only to the axial tip end side. In this case as well, water can be directed to the discharge opening 434. The gas sensor shown in FIG. 6 requires an additional process of forming the diameter expanded portion 436, but can contribute to increasing the design choice.

Hereinafter, the advantages of the present embodiment will be described.

As mentioned above, each of the side openings 432 is formed by protruding the guide 432a in the radial direction of the gas sensor 1, with the opening 432 being defined by the edge of the guide 432a. Each of the guides 432a introduces water so as to be directed to the axial tip end side, without permitting the water to be directed to the circumferential direction of the gas sensor 1 or toward the inner charge ports 412. The inventors of the present invention have found that this configuration can prevent the gas sensing element from getting wet with water and thus can prevent the cracks from occurring in the gas sensing element due to the water, while ensuring the responsiveness of the gas sensing element.

Figure 15:
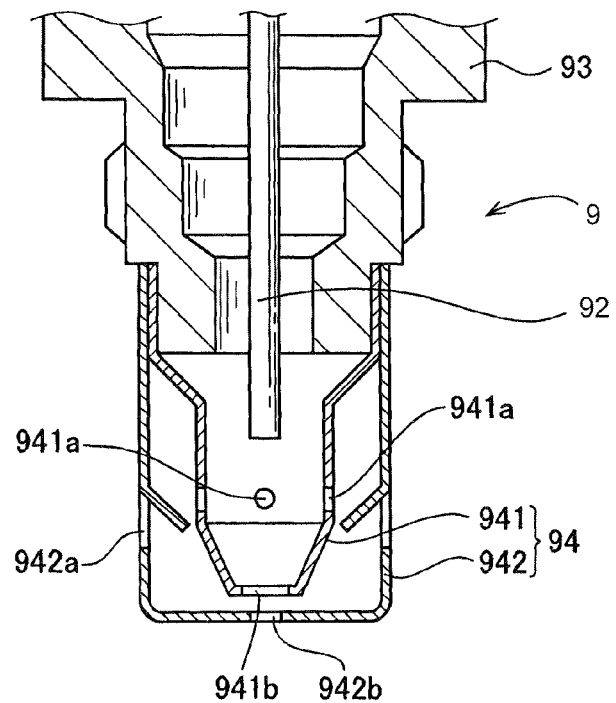
FIG. 15 is a vertical cross-sectional view illustrating the tip end portion of a gas sensor of a different mode according the conventional art.
Figure 16:
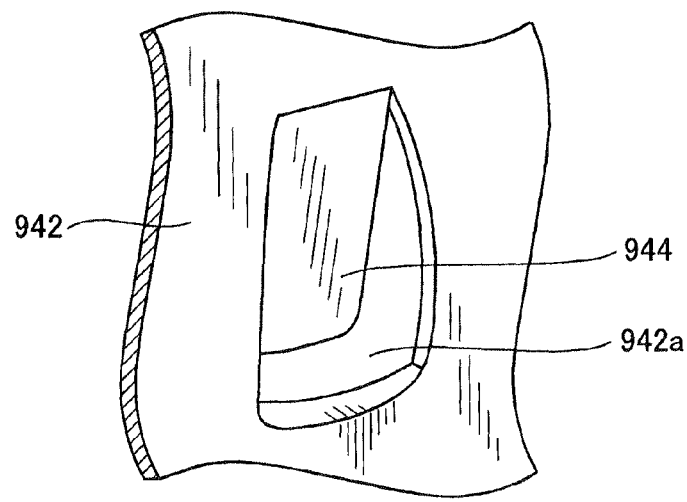
FIG. 16 is a perspective view illustrating a side opening of the gas sensor of the different mode according to the conventional art.

In other words, the side openings according to the conventional art (see reference 942a of FIG. 15) have been formed such that the opening direction of each of the side openings will have the components directed not only to the axial tip end side but also to the circumferential direction. Therefore, water that has entered into the outer cover (reference 942 of FIG. 15) together with the measurement gas may directly go into the circumferential direction and enter into the inner cover (reference 941 of FIG. 15) from the inner charge ports (reference 941a of FIG. 15), causing cracks in the gas sensing element (reference 92 of FIG. 15).

In this regard, with the present embodiment, the side openings 432 are each formed such that the guide 432a thereof can direct water to the axial tip end side, without permitting the water to be directed to the circumferential direction of the gas sensor 1 or toward the inner charge ports 412. Accordingly, the water that has entered into the drain cover 43 that is the outer cover can be sufficiently suppressed from moving in the circumferential direction in the interior of the drain cover 43 and from being directly directed to the inner charge ports 412.

Further, the side openings 432 each have the opening direction N which is imparted with the components directed to the axial tip end side. Accordingly, the water that has flowed with the measurement gas will first enter into the interior of the drain cover 43 from the side openings 432, but then will be directly directed, relatively linearly, to the tip end side with the force of inertia and discharged from the so discharge opening 434.

In the present embodiment, in particular, since the opening direction N does not have the components directed to the circumferential direction, water can be forcibly directed to the tip end side, whereby the advantageous effect as mentioned above can be remarkably exerted.

As a result, water can be well prevented from entering into the interior of the inner cover 41 to well prevent the occurrence of cracks in the gas sensing element 2 due to the water.

Meanwhile, the measurement gas having specific gravity comparatively smaller than the water will first enter into the interior of the drain cover 43 together with the water. Then, a part of the measurement gas will flow relatively linearly with the water toward the discharge opening 434, while a part of the measurement gas will flow separate from the water. The measurement gas that has flowed separate from the water flows, drawing a curve, toward the direction opposite to the discharge opening 434, i.e. toward the base end side. Thus, the interior of the drain cover 43 will be sufficiently filled with the measurement gas. Accordingly, the measurement gas can be well introduced into the inner cover 41 and thus can be well introduced to the gas sensing element 2.

As a result, responsiveness similar to that of the gas sensor 1 based on the conventional art can be ensured.

Further, the element cover 4 has a double structure consisting of the inner cover 41 and the drain cover 43 that is the outer cover 42. Owing to such a simple structure of the element cover 4, the gas sensor 1 of the present embodiment can reduce the cost, and can prevent the gas sensing element 2 from getting wet with water and thus can prevent the occurrence of cracks in the gas sensing element 2 due to the water, while ensuring its responsiveness.

Also, each of the side openings 432 has the opening direction N which is directed only to the discharge opening 434. Thus, since water so can be more easily discharged from the discharge opening 434, the gas sensor 1 of the present embodiment is more unlikely to suffer from cracks in the gas sensing element 2, which would be caused by getting wet with water.

The side openings 432 are each integrally formed together with the side wall body 431. Thus, the drain cover 43 can be formed without using additional members, to thereby enhance the productivity of the gas sensor 1 of the present embodiment.

The drain cover 43 has the guides 432a in the side wall body 431, which are each formed by inwardly protruding the drain cover 43 in the radial direction to thereby form the respective side openings 432 at the tip end portion thereof. Thus, as described above, the side openings 432 and the respective guides 432a can be easily formed by unidirectionally cutting the side wall body 431, followed by inwardly pressing the cut portion using a pressing jig that has a shape inverse of that of the guide 432a.

Further, each guide 432a is formed so that the profile line 432b as appears in a cross section thereof parallel to the axial direction of the guide 432a will be inwardly directed in the radial direction of the gas sensor 1 as the profile line nears the tip end side of the guide 432a. Thus, the measurement gas and water can be introduced into the drain cover 43 along the shape of the guide 432a, whereby the advantageous effect of the present invention can be more effectively exerted.

Each side opening 432 has the opening depth D of 0.5 mm or more and 1.5 mm or less. The opening depth D corresponds to the length from the outermost side portion of the side opening 432 to the innermost side portion thereof in the radial direction of the gas sensor 1. Further, each side opening 432 has an opening height H of 0.6 mm or less. The opening height H corresponds to the length from the very base end portion of the side opening 432 in the side wall body 431 to the very tip end portion thereof. Thus, the gas sensor 1 of the present embodiment will have good responsiveness and can further prevent the occurrence of cracks that would be caused by the water introduced into the interior of the inner cover 41.

In addition, the inner charge ports 412 are formed on the base end side in relation to the side openings 432. Thus, water and a part of the measurement gas are linearly directed to the discharge opening 434, while most of the measurement gas separated from the water is directed, drawing a curve, toward the base end side and then is introduced into the inner cover 41 from the inner charge ports 412. Therefore, the gas sensor 1 is well ensured with water resistance, and at the same time will have good responsiveness.

As described above, the gas sensor according to the present embodiment can prevent the gas sensing element from getting wet with water and thus can prevent the occurrence of cracks in the gas sensing element, which cracks would otherwise be caused by the water.

First Comparative Experiment

Hereinafter, a first comparative experiment will be described. It should be appreciated that, in the first and the subsequent comparative experiments, the identical or similar components to those in the above embodiment are given the same reference numerals for the sake of omitting explanation.

As shown in FIGS. 7 to 10, in the present comparative experiment, evaluation was made as to the responsiveness of gas sensors as well as the tendency in gas sensing elements to get wet with water (hereinafter referred to as "wettability").

Specifically, in the present experiment, four samples were prepared for each of three types of gas sensors, i.e. a gas sensor according to the above embodiment (hereinafter referred to as an "inventive product"), which will be described later, a comparative product 1 and a comparative product 2. These samples were tested to evaluate the responsiveness.

As the inventive product, the gas sensor as illustrated in FIG. 1 was prepared. Specifically, the inventive product had the outer cover, i.e. the drain cover, which was provided with the side openings and guides, each guide having a substantially triangular pyramid shape. Eight such side openings were circumferentially formed in the cylindrical side wall body of the drain cover. Each of the guides had an opening depth of 1 mm, an opening width of 2 mm, and an opening length of 3.8 mm which corresponded to the length from the base end portion to the tip end portion of the guide. Further, the inner discharge port of the inner cover had a diameter of 1 mm. Six inner charge ports, each having a diameter of 1.5 mm, were formed in the inner cover. The inner charge ports were arranged near the base end side in relation to the side openings.

The comparative product 1 was prepared based on the gas sensor illustrated in FIG. 1. Specifically, the comparative product 1 was provided with the side openings each having an opening direction which is imparted with the components directed not only to the axial tip end side but also to the circumferential direction. More specifically, the guides formed in the drain cover of the comparative product 1 were each provided with a louver having no side wall body portions. The opening depth of the louver was 0.5 mm. Other dimensions, such as the opening width, the opening length and the diameter of the inner discharge port of the comparative product 1 were the same as those of the inventive product. Further, the configuration other than the element cover was also the same as that of the inventive product.

Figure 14:
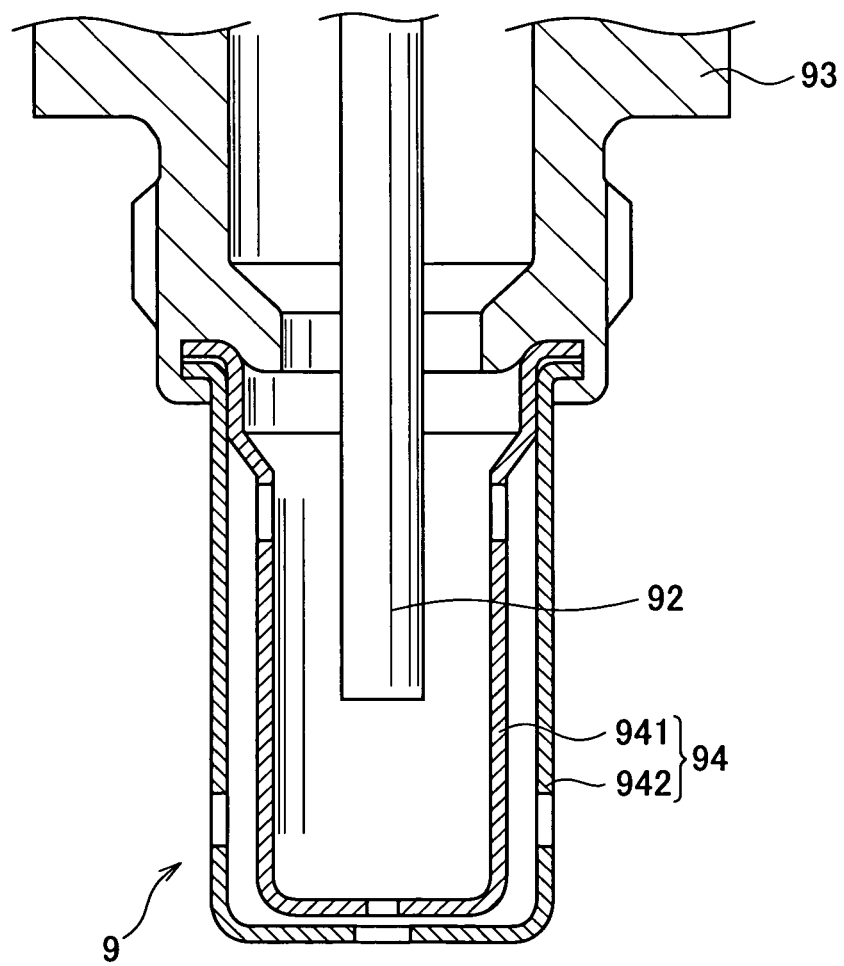
FIG. 14 is a vertical cross-sectional view illustrating a tip end portion of a gas sensor according to the conventional art.

As the comparative product 2, the gas sensor as illustrated in FIG. 14 was prepared. Specifically, the comparative product 2 had the substantially cylindrical inner cover and the substantially cylindrical outer cover. More specifically, the comparative product 2 had the inner cover and the outer cover, whose cylindrical side wall bodies were provided with the inner charge ports and outer charge ports, respectively. The inner charge ports were arranged near the base end side in relation to the outer charge ports. Each inner charge port of the inner cover had a diameter of 2.5 mm and each outer charge port of the outer cover had a diameter of 3.0 mm. The configuration other than the element cover was the same as that of the inventive product.

Figure 7:
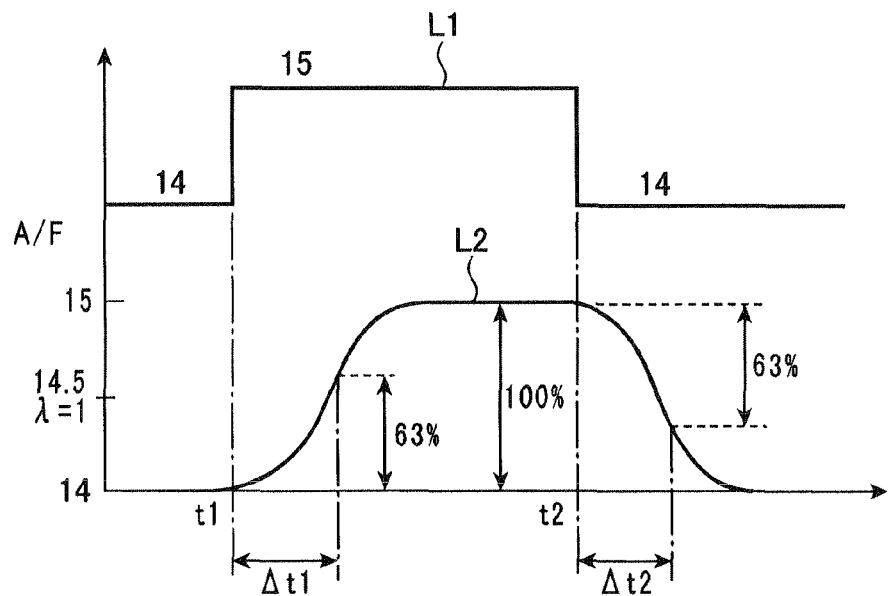
FIG. 7 is an explanatory view illustrating experimental methodology of responsiveness evaluation tests conducted in a first comparative experiment of the present invention.
Figure 8:
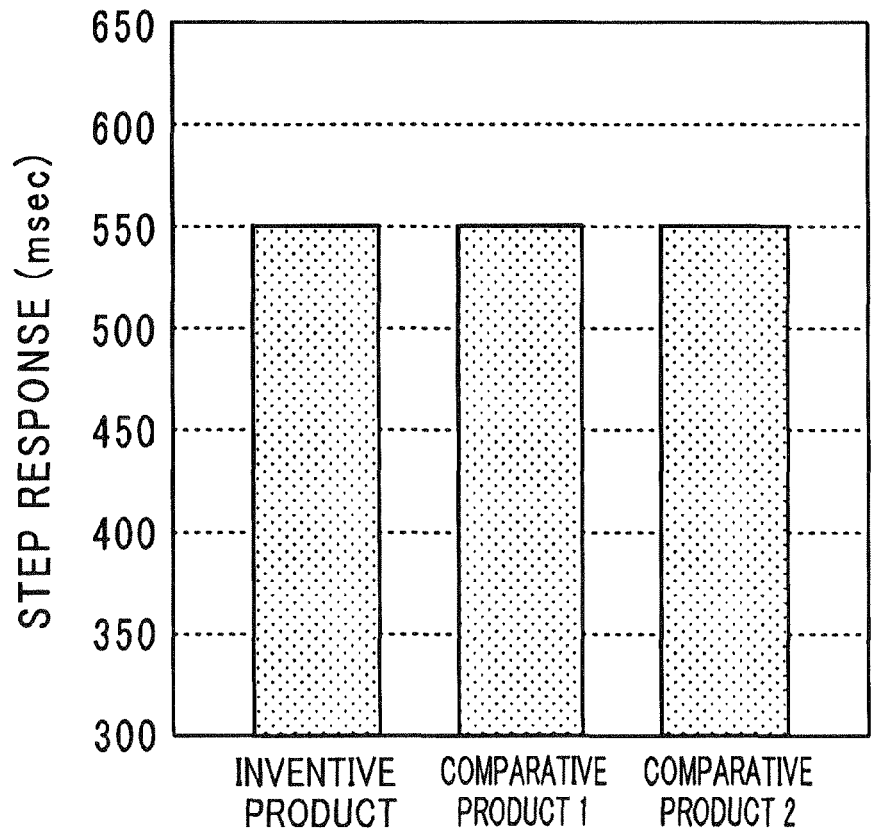
FIG. 8 illustrates the results of the responsiveness evaluation tests conducted in the first comparative experiment.

As shown in FIGS. 7 and 8, responsiveness as gas sensor was compared between the inventive product, the comparative product 1 and the comparative product 2.

Specifically, each of the above gas sensors was installed in an exhaust pipe of an in-line six-cylinder direct injection engine. The engine was operated at an engine speed of 1000 rpm.

As indicated by a line L1 in FIG. 7, in the engine, a state where an air-fuel ratio A/F was 14 and a state where the air-fuel ratio A/F was 15 were alternated a plurality of times.

The temperature of the gas sensing element was 750° C.

Under these conditions, the A/F values actually measured by the gas sensors of the inventive product, the comparative product 1 and the comparative product 2 were checked. Specifically, as indicated by a curved line L2 of FIG. 7, when the air-fuel ratio of the engine shifted from 14 to 15 at time t1, the time required for each A/F value to be increased by 63% (for each A/F value to reach 14.63) from time t1 in the course of the shifting from 14 toward 15, was measured. The difference between the measured time and time t1 was calculated as response time Δt1.

Also, when the air-fuel ratio of the engine shifted from 15 to 14 at time t2, the time required for each A/F value to be decreased by 63% (for each A/F value to reach 14.37) from time t2 in the course of the shifting from 15 toward 14, was measured. The difference between the measured time and time t2 was calculated as response time Δt2.

The above measurements were repeated a plurality of times to calculate an average value of the response times, for comparison with the inventive product, the comparative product 1 and the comparative product 2.

FIG. 8 shows the results of evaluation of responsiveness.

As can be seen from FIG. 8, there is substantially no difference in the responsiveness between the inventive product, the comparative product 1 and the comparative product 2.

It is considered that even when the flow rate of the measurement gas is changed or the shape of the element cover is changed, the same results as in the present experiment will be obtained.

Figure 9:
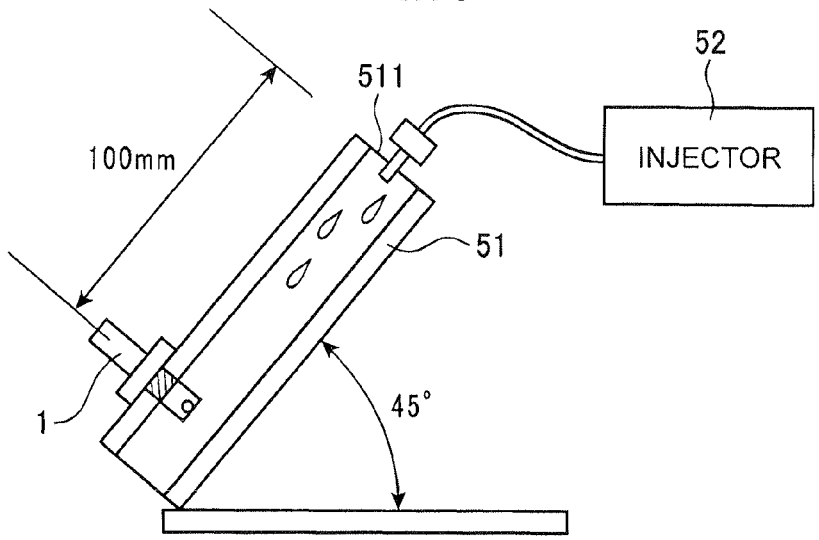
FIG. 9 is an explanatory view illustrating experimental methodology of wet evaluation tests conducted in the first comparative experiment.
Figure 10:
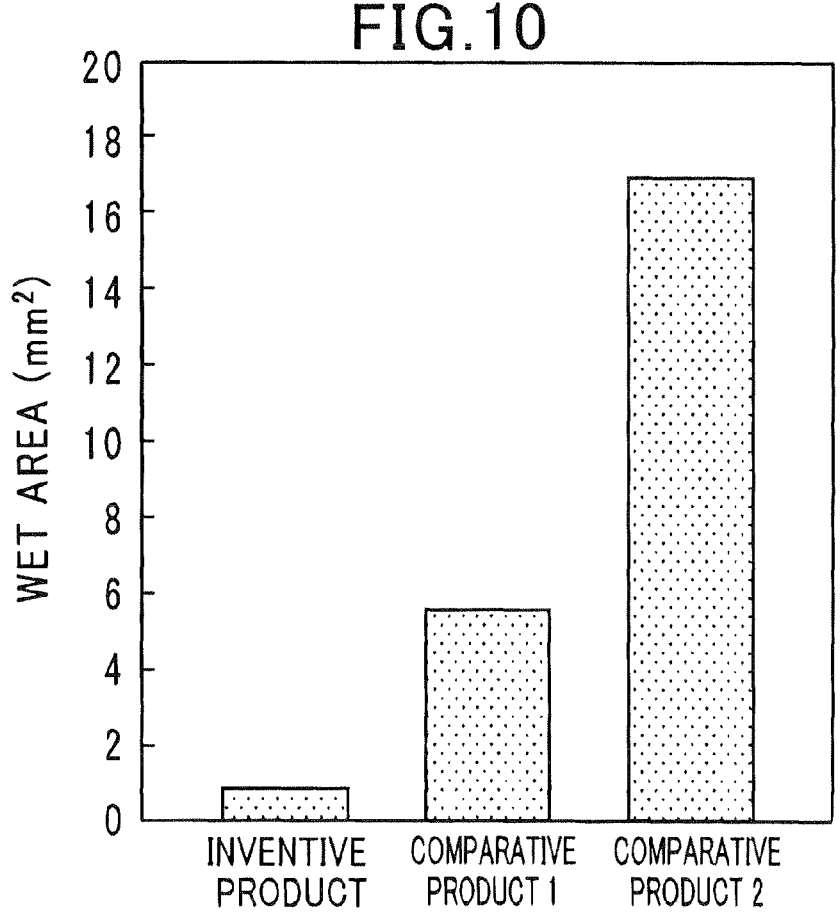
FIG. 10 illustrates the results of the wet evaluation tests conducted in the first comparative experiment.

As shown in FIGS. 9 and 10, evaluation tests were carried out as to whether or not water droplets would attach to the gas sensing element of the gas sensors of the inventive product, the comparative product 1 and the comparative product 2.

Specifically, as shown in FIG. 9, the gas sensor 1 prepared for each of the inventive product, the comparative product 1 and the comparative product 2 was disposed at piping 51 having an inner diameter of 35 mm and an inclination of 45° with respect to the horizontal plane, so that the gas sensor would be perpendicular to the piping 51. The position of installing the gas sensor 1 was 100 mm from an upper end opening 511 of the piping 51. Air that contains water droplets was injected five times from the upper end opening 511 using an injector 52. The amount of water in the injected air per one injection was 0.2 mL and air pressure was 0.15 kg/cm$^2$.

Then, the area got wet with water (hereinafter referred to as a "wet area") in the gas sensing element arranged in the element cover was measured.

Specifically, black carbon powder was coated on the surface of the gas sensing element prior to injecting water. Since the carbon powder would be separated from the portions got wet with water in the surface of the gas sensing element, the total area of these portions was calculated as the wet area.

In the present experiment, wettability was evaluated according to the size of the wet area. In this case, reference was made to the fact that no cracks would be substantially caused if the wet area was 3 mm$^2$ or less.

FIG. 10 shows the results of evaluation of wettability.

As can be seen from FIG. 10, compared to the comparative products 1 and 2, the inventive product could drastically reduce the wet area to 0.8 mm$^2$.

On the other hand, it will be understood that the comparative products 1 and 2 had large wet areas of 5.5 mm$^2$ and 17 mm$^2$, respectively.

It will be understood from the results of the present experiment that the inventive product is able to well suppress the occurrence of cracks in the gas sensing element, which would be caused by getting wet with water, while well ensuring the responsiveness of the gas sensor.

Second Comparative Experiment

Hereinafter, a second comparative experiment will be described.

Based on the gas sensor of the first embodiment, various gas sensors having different opening depth D and different opening height H in the side openings 432 were prepared to conduct the same wet tests as in the first comparative experiment.

Specifically, four samples were prepared for each of gas sensors having the opening depth D that fell within a range of 0.2 to 1.5 mm and the opening height H that fell within a range of −0.5 to 2 mm.

Figure 11A:
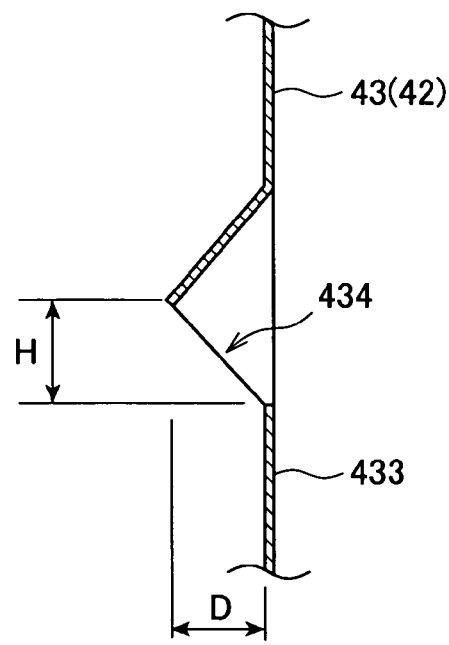
FIG. 11A is an explanatory view illustrating an opening height of a side opening used in a second comparative experiment of the present invention.
Figure 11B:
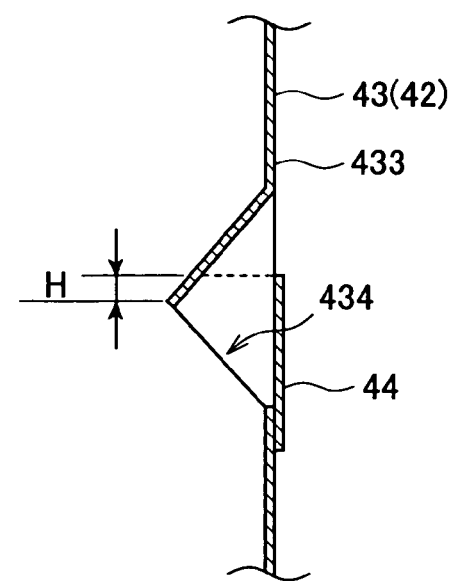
FIG. 11B is an explanatory view illustrating an opening height of the side opening in a state where the opening is covered with a shield member, in the second comparative experiment.

More specifically, as shown in FIG. 11B, the gas sensors were prepared by providing a shield plate 44 and displacing the shield plate 44 little by little over each side opening 432 having the opening height H of 2 mm to variably change the opening height H. As shown in FIG. 11B, the opening height H will have a minus value when the base end portion of the shield plate 44 is positioned near the base end side in relation to the base end portion of each side opening 432.

Figure 12:
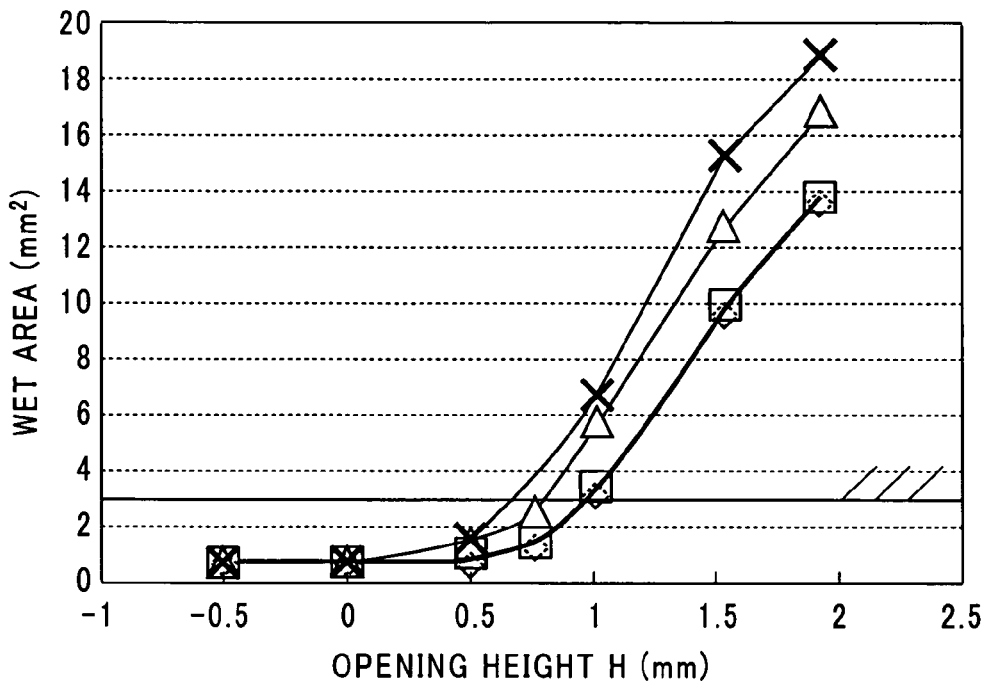
FIG. 12 illustrates the results of wet evaluation tests conducted in the second comparative experiment.

FIG. 12 shows the results of evaluation, in which a symbol "x" represents a gas sensor whose opening depth D was 1.5 mm, a symbol "Δ" represents a gas sensor whose opening depth D was 1.0 mm, a symbol "□" represents a gas sensor whose opening depth a was 0.5 mm and a symbol "◊" represents a gas sensor whose opening depth D was 0.2 mm.

As can be seen from FIG. 12, when the opening depth D was 1.5 mm or less and the opening height H was 0.6 mm or less, the wet area was 3 mm$^2$ or less and thus good enhancement was achieved in the water resistance of the gas sensing element.

On the other hand, it will be understood that, when the opening height H exceeded 0.75 mm, the wet areas drastically increased with the increase of the opening height H and thus it became difficult to attain higher water resistance.

As a result of the tests, it will be understood that, from the viewpoint of water resistance, a desirable opening depth D is 1.5 mm or less and a desirable opening height H is 0.6 mm or less.

Third Comparative Experiment

Hereinafter, a third comparative experiment will be described.

Based on the gas sensor of the first embodiment, various gas sensors having different opening depth D were prepared to evaluate the responsiveness.

Specifically, four samples were prepared for each of gas sensors having the opening depth D that fell within a range of 0.25 to 1.5 mm. Tests of responsiveness were conducted of these gas sensors.

The evaluation method for responsiveness was the same as the one used in the first comparative experiment.

The configuration of each gas sensor other than the opening depth D was the same as the configuration used in the second comparative experiment.

Figure 13:
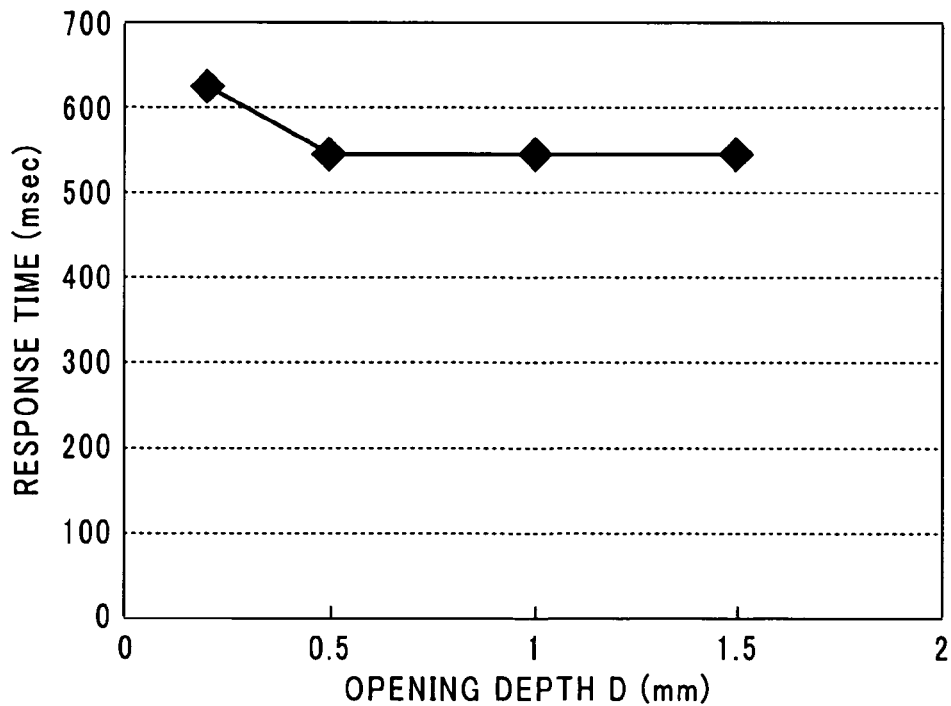
FIG. 13 illustrates the results of wet evaluation tests conducted in a third comparative experiment of the present invention.

FIG. 13 shows the evaluation results.

As can be seen from FIG. 13, when the opening depth D was 0.5 mm or more, the response time was about 550 msec and thus good responsiveness could be ensured.

On the other hand, it will be understood that, when the opening depth D was 0.5 mm or less, the response time gradually increased.

As a result of the tests, it will be understood that, with the opening depth D of 0.5 mm or more, the responsiveness of the gas sensor can be ensured.

The present invention may be embodied in several other forms without departing from the spirit thereof. The embodiment and modifications described so far are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A gas sensor comprising:
    a gas sensing element that senses a concentration of a specific gas contained in a gas to be measured;
    a housing that houses the gas sensing element such that the gas sensing element passes the housing therein; and
    an element cover secured to an end of the housing, wherein
    the element cover comprises an inner cover covering the gas sensing element and one or more outer covers disposed outside the inner cover,
    the at least one outer cover comprises an outer charge port that allows the gas to be introduced into the outer covers,
    the inner cover comprises an inner charge port that allows the gas to be introduced into the inner cover and an inner discharge port that discharges the gas to be measured to an outside of the gas sensor,
    the at least one outer cover includes one drain cover comprising a side opening functioning as the outer charge port and a discharge opening discharging the gas introduced into the drain cover, the side opening being formed through an approximately cylindrical side wall body, the discharge opening being formed through a bottom body formed on a tip end side of the side wall body, the inner charge port is formed closer to a base end than the side opening is, and the side opening is formed such that an opening direction directed from an outside of the drain cover to an inside of the drain cover has a directional component directed towards a tip end side in an axial direction of the gas sensor, wherein the side opening is integrally formed with the side wall body, and the drain cover has a recess formed at the side wall body by having the side wall body recessed towards a radially inside of the drain cover, wherein the side opening is formed adjacent to a tip end of the recess in the axial direction.

2. The gas sensor of claim 1, wherein the side opening has an opening depth defined as a radial distance at the side wall body, the radial distance being from an outermost portion of the side opening to an innermost portion of the side opening in the radial direction of the gas sensor, and an opening height defined as an axial distance at the side wall body, the opening height being from a portion of the side opening closest to the tip end of the gas sensor to a portion of the side opening closest to the base end of the gas sensor in the axial direction, wherein the opening depth is 1.5 mm or less and the opening height is 0.6 mm or less.

3. The gas sensor of claim 2, wherein the side opening has the opening depth which is 0.5 mm or more.

4. The gas sensor of claim 1, wherein the side opening is formed such that an inside of the drain cover cannot be seen when viewing the side opening along a direction perpendicular to the axial direction from outside the drain cover.

* * * * *